United States Patent
Jang et al.

(10) Patent No.: US 7,755,031 B2
(45) Date of Patent: Jul. 13, 2010

(54) CALIBRATION PHANTOM FOR QUALITY ASSURANCE OF IMAGE-BASED RADIOTHERAPY APPARATUS

(75) Inventors: Hong Seok Jang, Seoul (KR); Hoi Nam Kim, Seoul (KR); Tae Suk Suh, Seoul (KR); Ji Na Chang, Gyeonggi-do (KR); Seoung Jong Oh, Seoul (KR); Won Kyun Jung, Gyeonggi-do (KR); Teak Kwon Kim, Gyeonggi-do (KR)

(73) Assignee: Catholic University Industry Academic Cooperation Foundation, University ( * ) Notice: Subject to any disclaimer, the term of this patent is extended or adjusted under 35 U.S.C. 154(b) by 19 days.

(21) Appl. No.: 12/349,322

(22) Filed: Jan. 6, 2009

(65) Prior Publication Data

US 2009/0190723 A1 Jul. 30, 2009

(30) Foreign Application Priority Data

Jan. 25, 2008 (KR) ...................... 10-2008-0008034

(51) Int. Cl.
G01D 18/00 (2006.01)
(52) U.S. Cl. ...................... 250/252.1; 378/208; 378/205
(58) Field of Classification Search ............... 250/252.1; 378/208, 205, 4, 20
See application file for complete search history.

(56) References Cited

U.S. PATENT DOCUMENTS

| | | | | |
|---|---|---|---|---|
| 4,692,704 A | * | 9/1987 | Gray | ........................... 324/318 |
| 5,056,130 A | * | 10/1991 | Engel | ........................ 378/207 |
| 5,793,835 A | * | 8/1998 | Blanck | .......................... 378/4 |
| 6,831,269 B2 | * | 12/2004 | Zyromski | ................. 250/252.1 |
| 2004/0227069 A1 | * | 11/2004 | Sendai et al. | ............ 250/252.1 |
| 2005/0008126 A1 | * | 1/2005 | Juh et al. | ..................... 378/207 |
| 2005/0281478 A1 | * | 12/2005 | Kaufman et al. | ............ 382/260 |

\* cited by examiner

*Primary Examiner*—David P Porta
*Assistant Examiner*—Jessica L Eley
(74) *Attorney, Agent, or Firm*—Law Offices of Robert F. Zielinski, LLC

(57) ABSTRACT

A calibration phantom for quality assurance of an image-based radiotherapy apparatus The calibration phantom includes a body comprising a cylindrical acryl member having a predetermined diameter, the body having a center hole at a center axis thereof and a plurality of through-holes in outer circumferential portions thereof at a predetermined interval from the center hole; round stick-type density bars inserted into corresponding through-holes of the body and made of materials each with different densities; an acrylic cover detachably coupled with both ends of the body and having the same diameter as the body; and a plurality of bolts closely fastening the body with the cover by extending through the cover and the body and coupling with the nuts and each made of different materials. The cross-sectional shapes of the density bars and bolts appear on the image scanned by the CT apparatus and the radiotherapy apparatus.

7 Claims, 11 Drawing Sheets

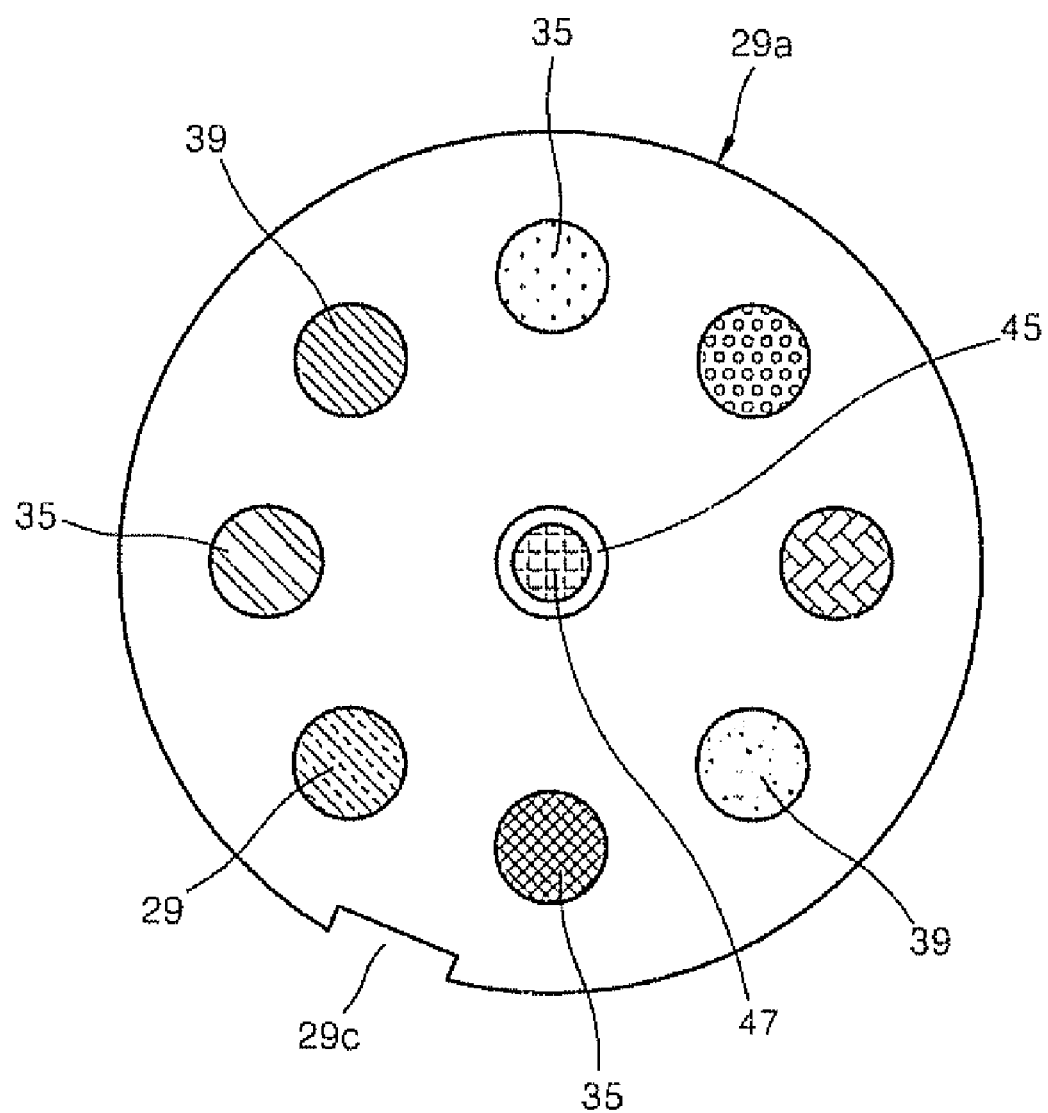

CALIBRATION PHANTOM FOR QUALITY ASSURANCE OF IMAGE-BASED RADIOTHERAPY APPARATUS

CROSS-REFERENCE TO RELATED PATENT APPLICATIONS

The present application claims priority to Korean Patent Application No. 10-2008-0008034, filed Jan. 25, 2008, the entire disclosure of which is hereby incorporated by reference

BACKGROUND OF THE INVENTION

1. Field of the Invention

The present invention relates to a calibration phantom for quality assurance of an image-based radiotherapy apparatus.

2. Description of the Related Art

With the rapid progress of scientific technology, medical devices are also rapidly progressing and previously impossible medical treatments and diagnoses are becoming possible one by one. Among these medical devices, there have been various kinds of imaging apparatuses to detect and diagnose the status of the patient's internal organs in detail.

Some examples of the imaging apparatuses are Computed Tomography (CT), Magnetic Resonance Imaging (MRI), Single Phonton Emission Computerized Tomography (SPECT), and Position Emission Tomography (PET) apparatuses. All of these apparatuses play very important roles in the diagnosis and treatment of tumors.

The imaging device is selected depending on the purposes of the diagnosis in order to capture accurate and clear images, since the imaging technologies of CT, MRI, SPECT, and PET are different from each other and they have their own advantages and disadvantages.

The CT apparatus is a device taking images based on the differences of the X-ray attenuation coefficient according to changes of electron density and provides good quality of anatomical imaging information with little distortion of images The CT is especially excellent for bone structure images and can be used as a basic prescriptive imaging device for radiotherapy since its density of information can be used to calculate the appropriate treatment volume and dosage Because the imaging apparatuses are designed to take the images of various kinds of tumors which are directly connected with a patient's survivability, accurate and precise imaging quality must be securely provided so that the doctors make a correct decision.

Therefore, the hospital with the imaging apparatuses needs to confirm if the devices are working properly. The procedures for the quality assurance of a series of medical imaging operations include a variety of measurement and evaluation which are continuously processed for system evaluation and system maintenance in order to secure the accuracy of a variety of information provided by the medical imaging devices.

The normal quality of the medical imaging devices slowly deteriorate as time goes by and the calibration processes must be done for continued quality assurance. A real cause for the quality changes of the devices needs to be reflected in the maintenance process after checking the image quality regularly or irregularly. Consequently, better quality of imaging products can be continuously provided by the devices and severe problems can be prevented from occurring before they happen.

After recognizing the size and location of the tumor via the medical imaging devices, radiotherapy using radiation can follow in order to remove the tumor. Radiotherapy is executed by an expensive medical device called a linear accelerator. The linear accelerator is used as a standard device for radiotherapy since the emitted energy can be minutely controlled as well as it delivers a high-dose-rate X-ray and an electronic beam.

While the linear accelerator is used, the most important thing is that radiation is collectively delivered to a tumor area without reaching a normal tissue area. Even though an accurate treatment plan has been established, it cannot be completely prevented that radiation damages normal tissues because the status of the tumor, located inside the patient's body lying down on a couch during radiotherapy, cannot be observed in real time.

Accordingly, an image-based radiotherapy apparatus has been developed recently. The image-based radiotherapy apparatus is a kind of medical radiation treatment device combining an imaging device with a radiation treatment machine, and is expected to be the next generation radiotherapy apparatus because radiation treatment can be started without delay and radiation beam can be delivered to the target point accurately and while observing the status of the tumor located inside the patient's body lying down on the couch (without movement of the patient).

There is a problem with unestablished quality maintenance procedures up until now because the image-based radiotherapy apparatus is the latest, newest machine. There is no satisfactory quality maintenance system for ensuring the quality of the image-based radiotherapy device Therefore, the hospitals or the organizations using the newly installed treatment device create their own equipment or are supplied by the small/medium medical equipment companies with the equipment for conducting the quality assurance.

SUMMARY OF THE INVENTION

Accordingly, the present invention has been made keeping in mind the above problems occurring in the related art, and embodiments of the present invention provide a calibration phantom installed on an image-based radiotherapy apparatus for quality assurance of the image-based radiotherapy apparatus. The calibration phantom performs the quality assurance of an imaging device and a radiation treatment machine at the same time, and increases the treatment success rate by realizing the movement of the radiation treatment machine more precisely since the centers of the imaging device and the radiation treatment machine can be accurately adjusted.

In an exemplary embodiment of the present invention, the calibration phantom for quality assurance is placed on a couch of an image-based radiotherapy apparatus, which includes a Computed Tomography (CT) apparatus and a radiation treatment machine combined with the CT apparatus, and is provided for quality assurance of the CT apparatus and the radiation treatment machine based on an image scanned by the CT apparatus and the radiation treatment machine. The calibration phantom may include a body comprising a cylindrical acryl member having a predetermined diameter, wherein the body has a center hole at a center axis thereof and a plurality of through-holes in outer circumferential portions thereof at a predetermined interval from the center hole; round stick-type density bars inserted into corresponding through-holes of the body, with cross-sectional shapes thereof appearing on the image scanned by the CT apparatus and the radiotherapy apparatus, the density bars made of materials each with different densities, an acrylic cover detachably coupled with both ends of the body and having the same diameter as the body; and a plurality of bolts closely fastening the body with the cover by extending through the cover and the body and coupling with the nuts, with cross-sectional shapes thereof appearing on the image scanned by the CT apparatus and the radiotherapy apparatus, the bolts each made of different materials.

The calibration phantom for quality assurance may further include a disk-shaped plug inside the center hole, wherein the plug has disk-shaped multiple holes having different diameters, and is used for inspecting a resolution of the CT apparatus.

The calibration phantom for quality assurance may further include a bead in an internal central area of the center hole, wherein a cross section of the bead appears as a central point of the phantom on the image scanned by the CT apparatus and radiotherapy device.

The density bars and the bolts are made of any one selected from the group consisting of polyacetal, Monomer Cast (MC) nylon, acryl, polyethylene, polycarbonate, Teflon, polypropylene, and polyvinyl chloride.

The calibration phantom for quality assurance may further include a base at the bottom of the phantom so as to support the phantom on the couch.

Furthermore, at least one groove may be formed on an outer surface of the phantom, and the base may have an inclined plane at a predetermined angle towards a flat table of the couch; a plurality of fixing grooves formed on the inclined plane to support the phantom on the inclined plane; and a supporting block provided to support the phantom on the base, wherein the supporting block is inserted into the fixing groove while protruding from the inclined plane and is coupled into the groove of the outer surface of the phantom.

The top surface of the supporting block protruding from the top portion of the base is inclined at a predetermined angle towards the flat table in order to tilt the phantom placed on the base at a predetermined angle.

The phantom for quality assurance of an image-based radiotherapy apparatus of the present invention formed with the above mentioned figures is installed on the image-based radiotherapy apparatus to perform the quality assurance of the imaging apparatus and the radiation treatment machine at the same time, and can increase the treatment success rate by realizing the movement of the radiation treatment machine more precisely since the centers of the imaging apparatus and the radiotherapy device can be accurately adjusted.

BRIEF DESCRIPTION OF THE DRAWINGS

The above and other objects, features and advantages of the present invention will be more clearly understood from the following detailed description when taken in conjunction with the accompanying drawings, in which:

FIG. 5B is a cross-sectional view of the body shown in FIG. 5A taken by tomography;

DETAILED DESCRIPTION OF THE INVENTION

Figure 1:
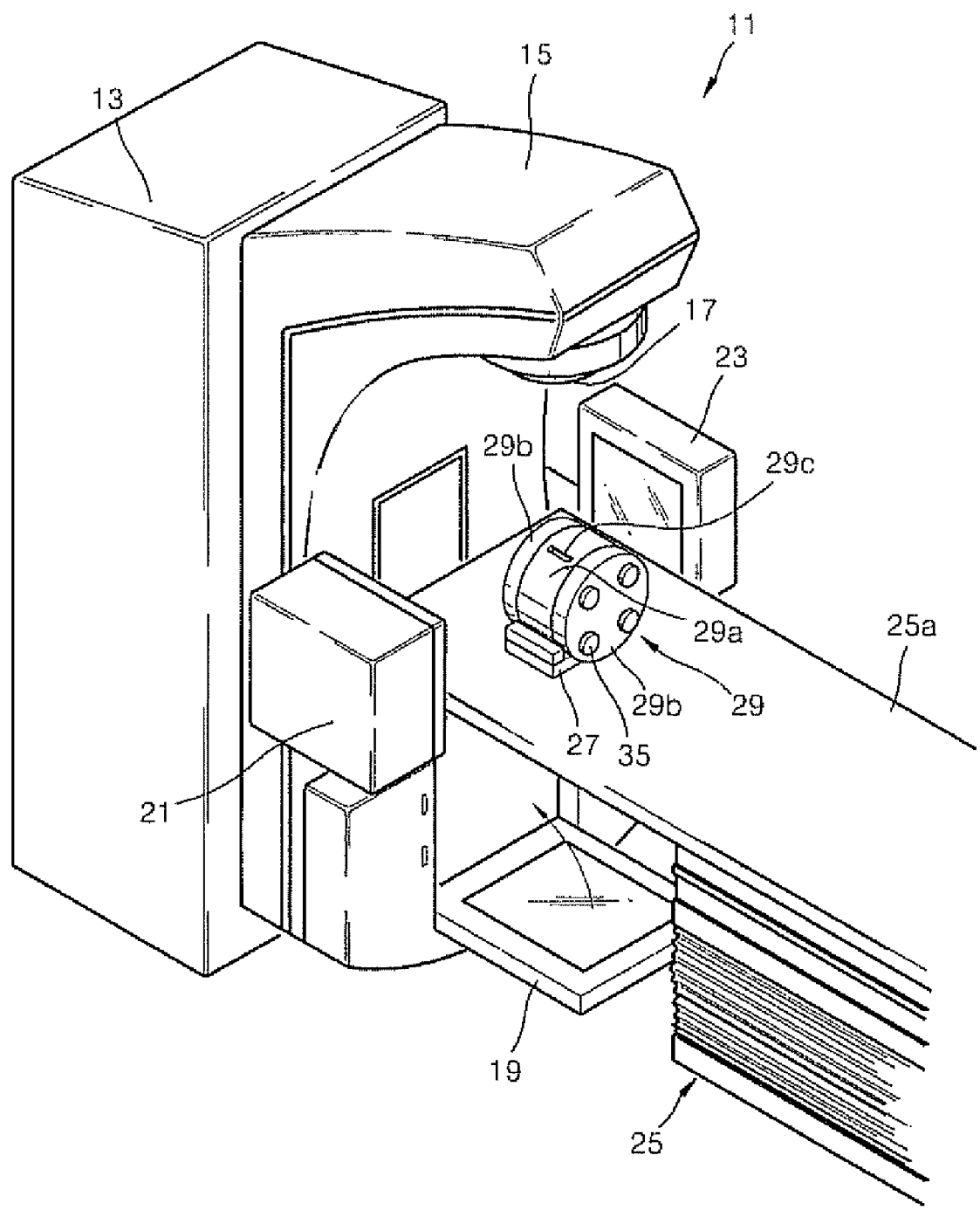
FIG. 1 is a prospective view illustrating a calibration phantom for quality assurance installed on an image-based radiotherapy apparatus in accordance with an embodiment of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 is a prospective view illustrating a calibration phantom 29 for quality assurance installed on an image-based radiotherapy apparatus 11 in accordance with an embodiment of the present invention.

Referring to the drawing, the calibration phantom 29 is placed on a couch 25 of the image-based radiotherapy apparatus 11.

First, the image-based radiotherapy apparatus 11 includes a body 13 perpendicularly fixed and a rotating gantry rotatably installed with the axis in front of the body 13. A high voltage generator, a microwave generator and the like are installed inside the body 13; an accelerating tube accelerating the electrons, a magnetic field generator, a radiation emission part 17 and the like are installed inside the rotating gantry 15. The radiation emission part 17 is a region emitting radiation to a target area.

A radiation detector 19 is installed at the bottom part of the rotating gantry 15 in the drawing. The radiation detector 19 plays a role to sense the radiation dose from the radiation emission part 17 and is used as an unfolded status during the quality assurance.

A linear accelerator is an example of the radiation emission device having the above mentioned configuration and this will be called a radiotherapy apparatus in the following description.

A Computed Tomography (CT) apparatus is installed at both ends of the rotating gantry 15. The CT apparatus includes a CT source 21 emitting X-rays and a CT detector 23 located opposite the CT source 21. The CT source 21 and the CT detector 23 are fixed at the sides of the rotating gantry 15 and take images of treatment target areas while rotating together with the rotating gantry 15. Hereinafter, the CT source 21 and the CT detector 23 are referred to collectively as the CT apparatus.

The couch 25 is a bed where a patient can lie down. A flat table 25a is movable in left and right directions as well as top and bottom directions One end of the flat table 25a is located between the radiation emission part 17 and the radiation detector 19, and supports the phantom 29 located thereon.

The phantom 29 is made of acryl and has a cylindrical shape on the whole. The cylindrically-shaped phantom 29 can be preferably supported by the base 27 not to roll down on the couch 25 The base 27 is made of acryl and stably supports the cylinder-shape phantom 29 on the couch 25.

The phantom 29 includes a cylinder body 29a having a certain diameter and thickness, a cover 29b tightly fixed on both ends of the body 29a, a plurality of bolts 35 fixing the cover 29b on the body 29a by passing through the cover 29b and the body 29a, and a plurality of density bars (39 in FIG. 3) inserted into the inside body 29a so as to express their cross-sectional shape when tomographically imaged by the CT apparatus. The drawing number 29c is a supporting groove, which will be described below.

Anyhow, the phantom 29 in accordance with the embodiment of the present invention is located on a vertically lower place of the radiation emission part 17, imaged by the CT apparatus and the radiation emission part 17 (simultaneously or respectively), and the image-based radiotherapy apparatus 11 can be quality assured via the images taken by the tomograph.

Figure 2A:
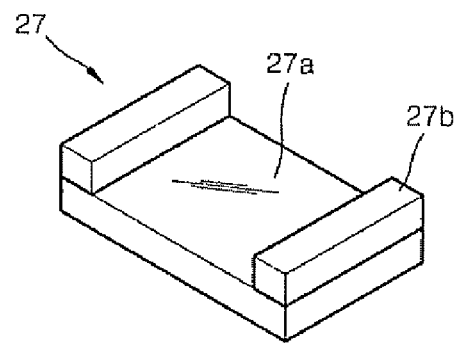
FIGS. 2A and 2B are prospective views illustrating the bases of the phantom shown in FIG. 1.
Figure 2B:
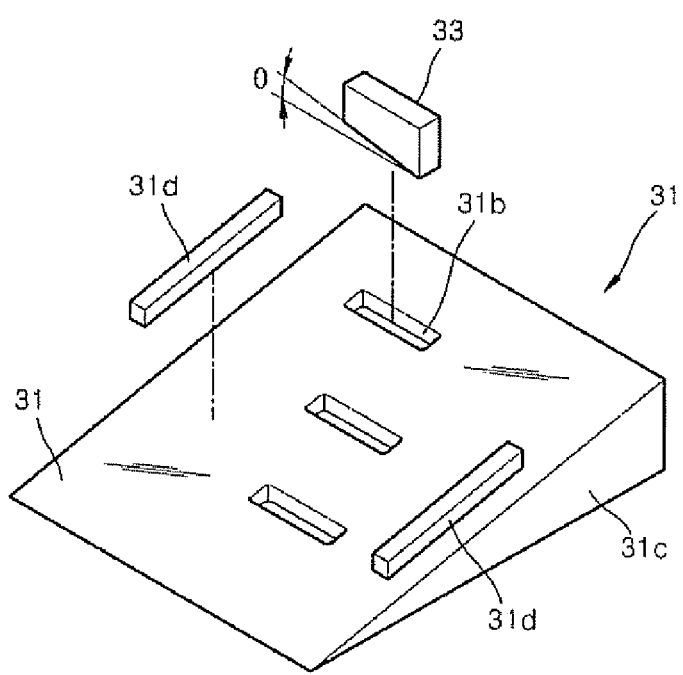

FIGS. 2A and 2B are prospective views illustrating the bases of the phantom 29 shown in FIG. 1.

There are basically two types of bases supporting the phantom 29 in accordance with the embodiment.

The base 27 shown in FIG. 2A includes a supporting panel 27a having a regular thickness and stumbling projections 27b fixed on the top of both ends of the supporting panel 27a. The stumbling projections 27b are in contact with the outer circumferential surface of the phantom 29 and support the phantom 29 so that it does not roll down from the supporting panel 27a.

The base 31 in FIG. 2B provides a tilted plane 31a at a certain angle towards the flat table 25a of the couch 25, and includes a tilted panel 31c having a plurality of fixing grooves 31b; a supporting block 33 inserted into one of the fixing grooves 31b; and a couple of square bars 31d, which is used when the supporting block 33 is not used. The square bar is a stick having a regular square cross-sectional shape in the longitudinal direction.

The supporting block 33 is projected on the top of the tilted plane 31a in a state of being inserted into the fixing groove 31b. Especially, the top surface of the supporting block 33 inserted into the fixing groove 31b is inclined at an angle θ towards the flat table. When the top portion of the supporting block 33 is inserted into the supporting groove (29c in FIG. 1) after inserting the supporting block 33 into the fixing groove 31b, the phantom is inclined at the angle θ as shown in FIG. 11. The reason why the phantom is slantingly placed will be described below.

While the supporting block 33 is slantingly supporting the phantom 29, the square bar 31d supports by horizontally lifting the phantom 29 in a state of being supported by the supporting block 33. It supports by horizontally lifting the phantom 29 as much as it maintains the state of being supported by the supporting block 33.

Figure 3:
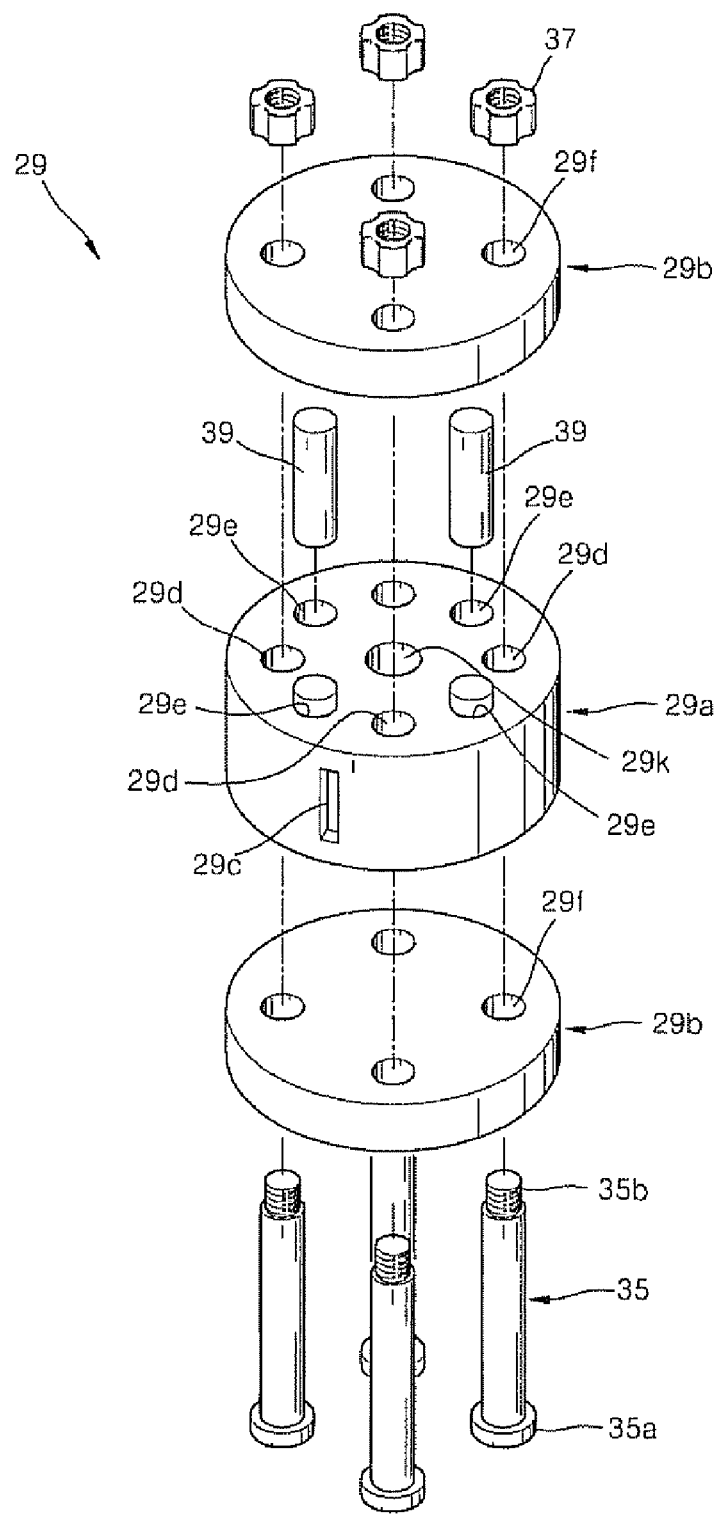
FIG. 3 is an exploded view of the calibration phantom for quality assurance in accordance with the embodiment of the present invention.

FIG. 3 is an exploded view of the calibration phantom for quality assurance in accordance with the embodiment of the present invention.

As shown in the drawing, the phantom 29 in accordance with the embodiment includes a cylindrical body 29a, a cover 29b tightly coupled with the both ends of the body 29a, a plurality of density bars 39 inserted into the body 29a, bolts 35 and nuts 37 coupling the cover 29b with the body 29a. The bolts 35 and the nuts 37 are made of different kinds of materials.

The body 29a is made of transparent or translucent acryl and has a center hole 29k at the central axis. The center hole 29k is a hollow having a regular diameter and passes through the body 29a. Four bolt holes 29d and four density bar holes 29e are formed at the outer part of the body 29a which is remote from the center hole 29k.

Each bolt hole is located between the density bar holes and separately located at the regular distance. The bolt hole 29d is a hole through which the bolt 35 passes. The density bar hole 29e is the hole fixing the density bar 39 via its insertion therein.

The density bar 39 is a round stick type member having a regular diameter and length, and fixed in the density bar hole 29e by insertion. Each of the four density bars 39 is made of a different kind of material. The bolt 35 has a regular diameter and is elongated in the longitudinal direction. A male screw part 35b is formed on its one end and a head part 35a is formed on the other end.

The cover 29b is a kind of disk type member containing a plug which will be described below (43 in FIG. 4A) or a glass bead (47 in FIGS. 5A and 5B) at the inside of the center hole 29k and supports the density bar 39 in the density bar hole 29e by being tightly fixed on both ends of the body 29a. The cover 29b is made of the same acryl as the body 29a and has four bolt holes 29f at the edges respectively.

The bolt holes 29f naturally correspond to the bolt holes 29d formed on the body 29a. Paths where the bolt 35 can pass through will be secured by matching the cover 29b with the bolt hole 29d and 29f while the cover 29b is placed on both sides of the body 29a.

Finally, the phantom setting can be finished by screwing each of the nuts 37 onto the male screw part 35b of a corresponding one of the bolts 35 after covering both ends of the body 29a with the cover 29b and then after passing the bolts 35 through the cover 29b, the body 29a, and the other side cover 29b in the state where the density bar 39 is inserted into the density bar hole 29e.

In the mean time, four density bars 39 and four bolts 35 are each made of a different kind of material. For example, each of the four density bars 39 and the four bolts 35 can choose any one of the following 8 kinds of materials: polyacetal, Monomer Cast (MC) nylon, acryl, polyethylene, polycarbonate, Teflon, polypropylene, and polyvinyl chloride. In addition, the bolt 35 and the nut 37 can be made of same material.

The density bar 39 and the bolt 35 are used for the quality assurance of the CT apparatus and this will be described next time.

Figure 4A:
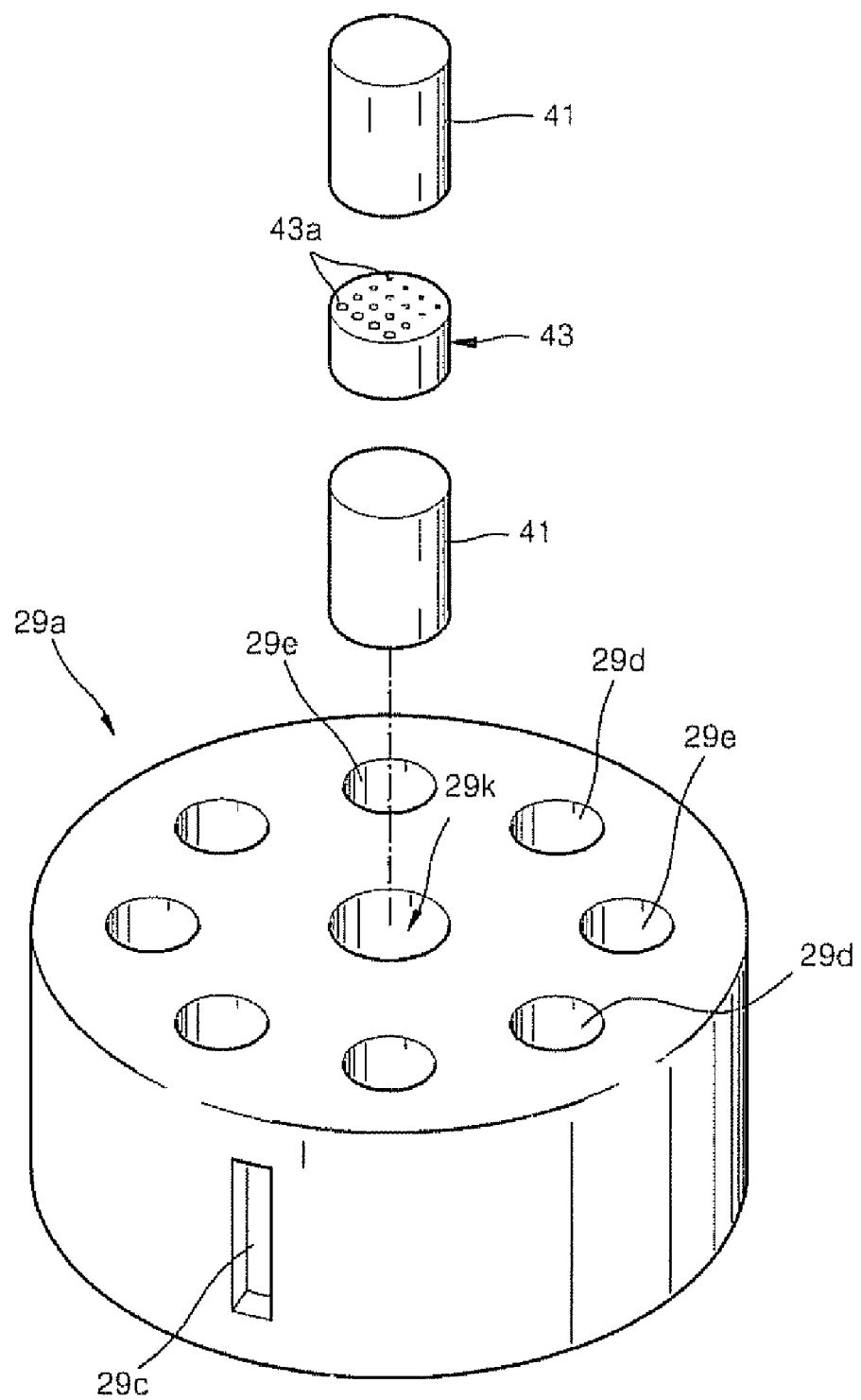
FIG. 4A is an exploded view for explaining one usage of the body of the calibration phantom for quality assurance shown in FIG. 3.
Figure 4B:
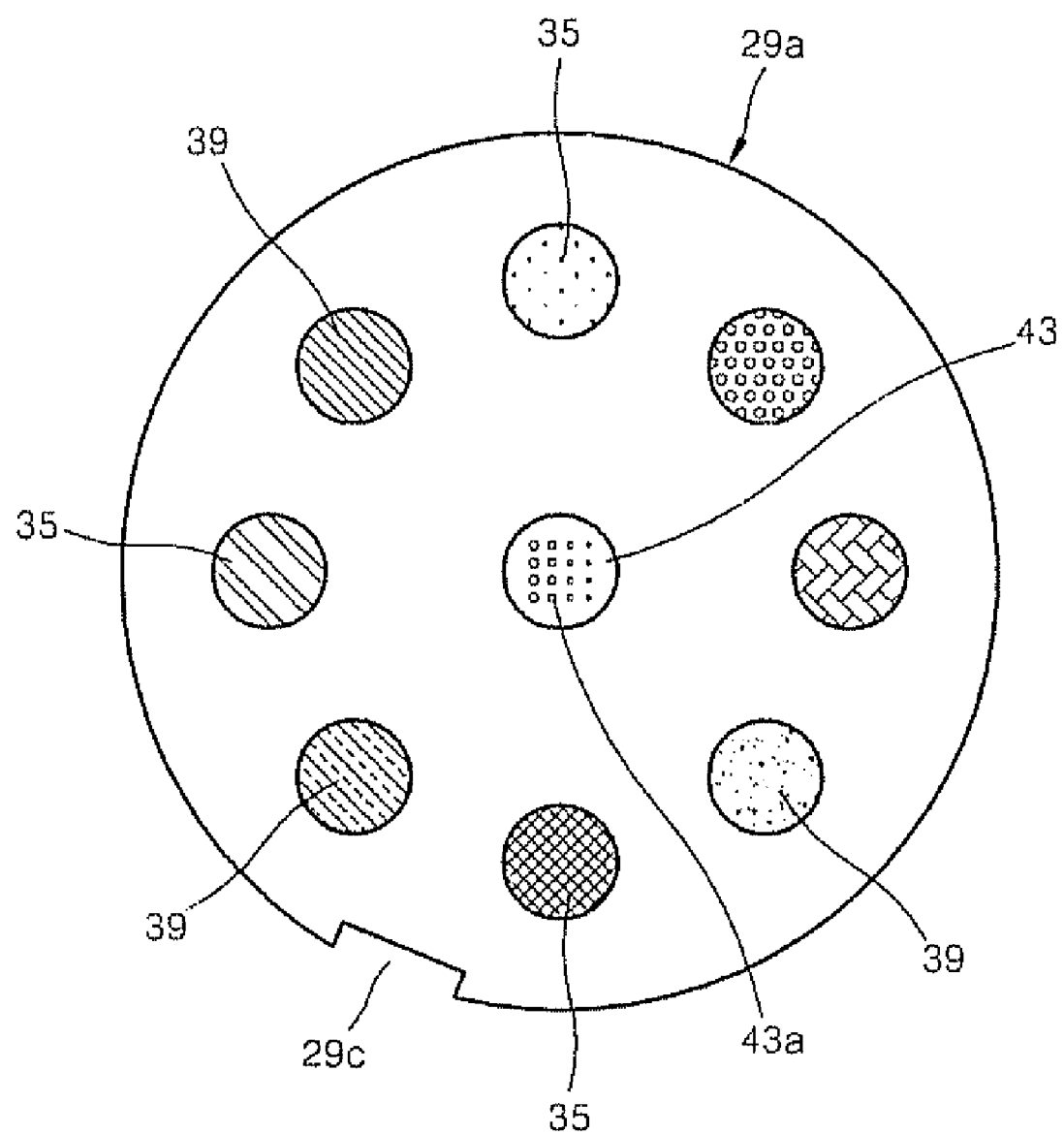
FIG. 4B is a cross-sectional view of the body shown in FIG. 4A, taken by tomography.

FIG. 4A is an exploded view for explaining one usage of the body of the calibration phantom for quality assurance shown in FIG. 3. The density bar (39 in FIG. 3) is omitted in the drawing.

Referring to the drawing, it is understood that the plug 43 can be installed inside the center hole 29k. The plug 43 is a kind of disk type member and is located at the center of the center hole 29k by a supporting member 41 The plug 42 functions to inspect the resolution of the CT apparatus.

The diameters of the sixteen holes 43a on the plug 43 can be processed to grow gradually from a smallest size of 0.4 mm up to 1.9 mm by a 0.1 mm increase per hole.

FIG. 43 is a schematic view of a tomographic image of the body 29a (in a state where the bolt 35 and the density bar 39 are inserted into the bolt hole 29d and the density bar hole 29e) shown in FIG. 4A taken by the CT apparatus As shown in the drawing, the cross-sectional shapes of the bolts 35 and the density bars 39 are viewed as different patterns. In the actual images, the cross-sectional shapes of the bolts and the density bars are recognized by the different levels of brightness. As everybody knows, when the substances having different densities are tomographically imaged by the CT apparatus, the differences of the densities are viewed as the differences of the brightness in the tomographic images. As the density is higher, the image becomes brighter and the substance with low density is shown as a darker image.

Through the tomographic images taken by the CT apparatus, the electron density of the density bar 39 and the bolt 35 displayed on the images can be calculated and compared to the densities of the actual density bar 39 and the actual bolt 35, and then it will be evaluated if the CT apparatus accurately recognizes the density of the target substances.

The shape of the plug 43 is shown in the drawing. A plurality of holes 43a formed on the plug 43 can be clearly shown or vaguely shown depending on the resolution of the CT apparatus. The resolution quality of the CT apparatus can be distinguished on the basis of the clarity of the holes 43a.

Figure 5A:
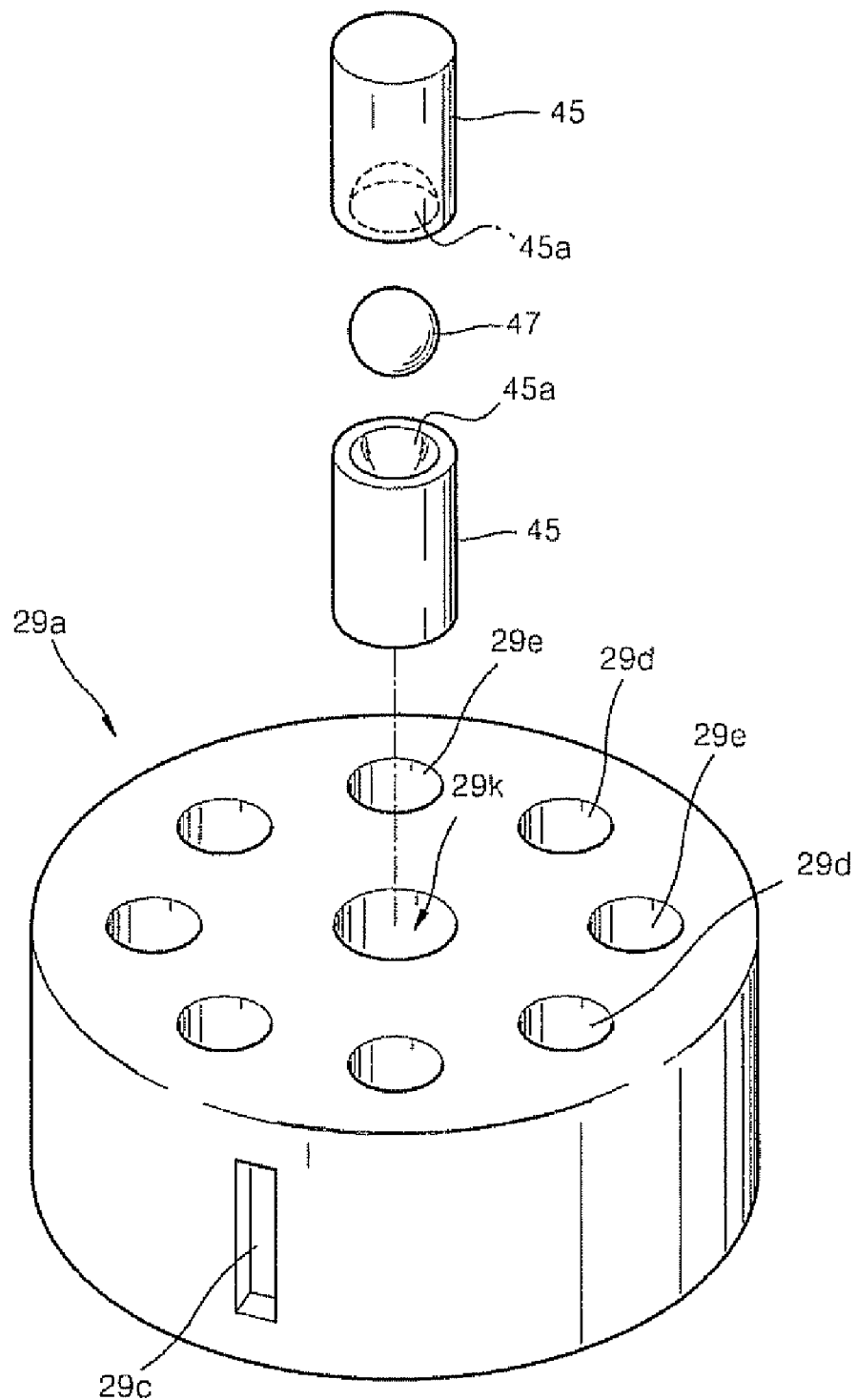
FIG. 5A is an exploded view explaining another usage of the body of the calibration phantom for quality assurance shown in FIG. 3.

FIG. 5A is an exploded view for explaining another usage of the body included in the calibration phantom for quality assurance shown in FIG. 3.

Referring to FIG. 5A, it is understood that a glass bead 47 can be installed at the center of the center hole 29k. The glass bead 47 plays a role as a reference point by being located at the center of the phantom 29. Two supporting members 45 are inserted together into the center hole 29k to fix the glass bead 47 at the correct position.

The supporting member 45 is a cylindrical member and closely sticks to the inner peripheral surface of the center hole 29k, and has two hemispheric grooves 45a on the opposing sides. The hemispheric grooves 45a are grooves to accept halves of the glass bead 47, respectively. The glass bead 47 will be accepted and fixed between two supporting member 45 by facing the supporting members 45 each other.

FIG. 5B is a cross-sectional view of the body (in the state where the bolt 35 and the density bar 39 are inserted into the bolt hole 29d and the density bar hole 29e as in FIG. 4A) shown in FIG. 5A taken by tomography.

As shown in the drawing, the cross-sectional shape of the glass bead 47 is viewed at the center of the cross-sectional shape of the body 29a. The position of the glass bead 47 is shown as a dot on a tomographic image taken by the CT apparatus and radiotherapy device. A radiotherapy device also can take the tomographic image of a target object by lowering the energy of generating X-ray.

The glass bead 47 plays a role as a reference point to adjust the center of the CT apparatus and radiotherapy device. In an image-based radiotherapy apparatus, the target point of the radiation emitted from the radiotherapy device needs to accurately correspond to the irradiation target point recognized from tomographic image by the CT apparatus and then accurate treatment can be accomplished. Verifying if the radiation emitted from the radiation emission part 17 accurately corresponds to the position of the glass bead 47 recognized by the CT apparatus is the most important part of the quality assurance process.

The process of executing the quality assurance is described below.

First, the calibration phantom 29, in which the glass bead 47 is installed, is placed at the vertical bottom of the radiation emission part 17. A tomographic image of the phantom 29 will be taken while the rotating gantry 15 is rotating 360 degrees in this state. The CT apparatus and the radiotherapy device take tomographic images of the phantom 29 with its own method while the rotating gantry 15 is rotating. The radiotherapy device is taking tomographic images in the state of lowering the generating energy and unfolding the radiation detector (19 in FIG. 1).

Once the taking of tomographic images by the CT apparatus and the radiotherapy device is finished, the images will be reorganized in the computer. Nine reference points are marked on the reorganized image. The reference points are eight points marked at the both ends of four density bars 29 and one point marked at the glass bead 47 The glass bead is marked as a dot on the reorganized image. Therefore, nine reference points are marked in total on the image.

Anyhow, nine reference points are marked on the monitor by matching the reorganized image from the CT apparatus and the reorganized image from the radiotherapy device. During the matching process, all the reference points can accurately overlap or cross each other in some parts or on the whole. When the reference points are crossed with each other, it means that the CT apparatus or the radiotherapy device is not working properly and that repairing the hardware or the software is needed.

Figure 6:
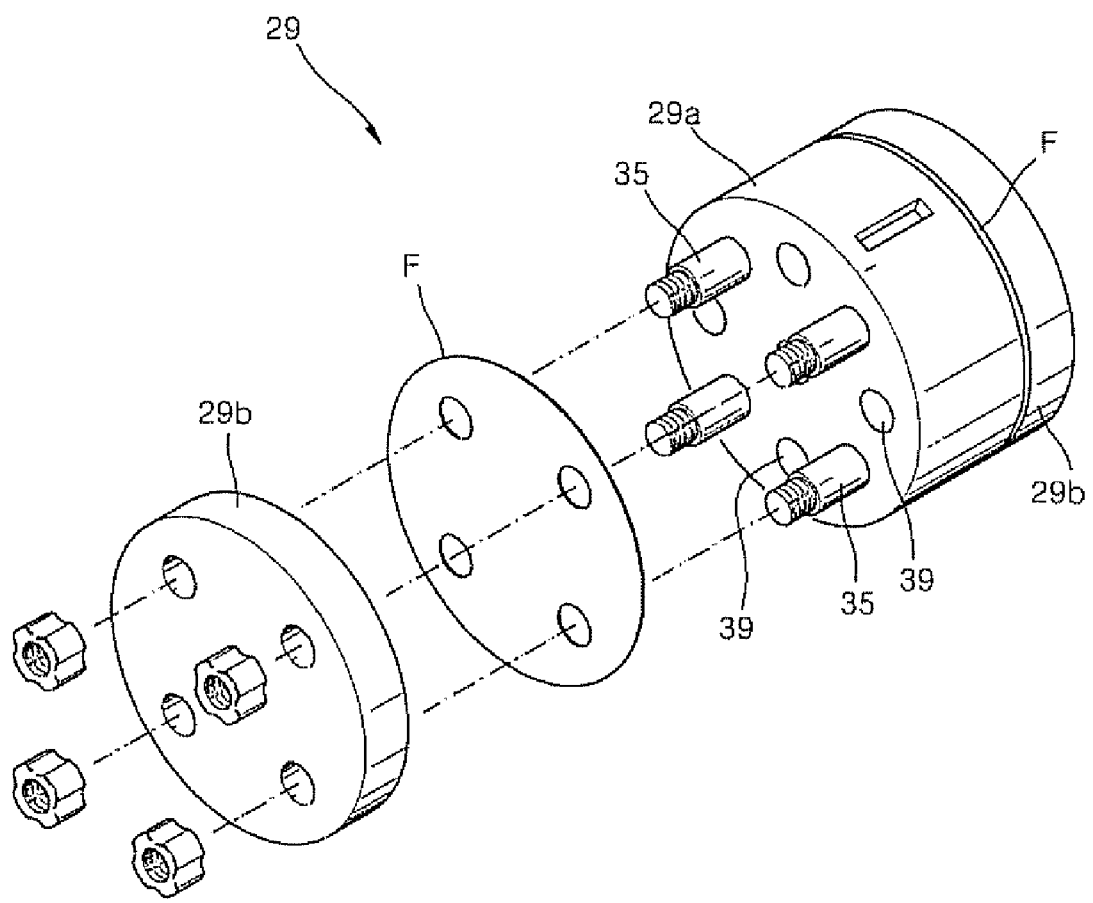
FIG. 6 is a perspective view illustrating an X-ray film applied to the calibration phantom for quality assurance shown in FIG. 3.

FIG. 6 is a perspective view illustrating an X-ray film applied to the calibration phantom for quality assurance shown in FIG. 3.

Since the phantom 29 in accordance with the embodiment has basically the structure of detachably fixing the cover on both ends of the body 29a, an X-ray film F can be inserted between the body 29a and the cover 29b depending on the necessity.

The X-ray film F can be used to check if the turning radius of the radiation emission part 17 rotating around the target point (T in FIG. 9) is stably maintained. As is common knowledge, the side of the radiation emission part 17 of the rotating gantry 15 is a heavier portion and can be slightly inclined towards the bottom direction. The X-ray film F can check this kind of mechanical error.

Radiation emitted from the radiation emission part 17 has a high energy to leave a trace on the X-ray film F and is emitted in a plane that matches with the plane having the X-ray film F.

Figure 7:
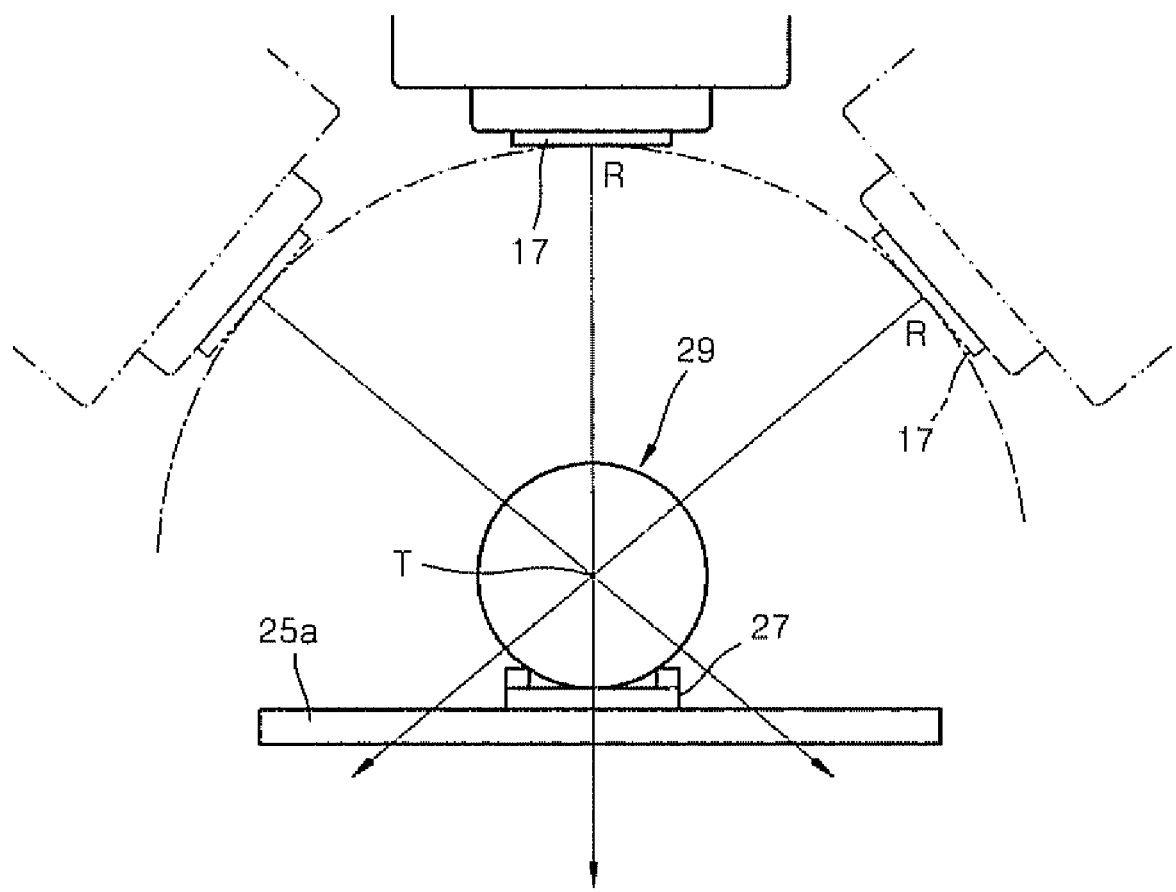
FIG. 7 is a view illustrating the state in which the quality assurance of the radiotherapy apparatus is performed using a calibration phantom for quality assurance in accordance with the embodiment of the present invention.

FIG. 7 is a view illustrating the state in which the quality assurance of the radiotherapy device is performed using a calibration phantom for quality assurance in accordance with the embodiment of the present invention.

Referring to FIG. 7, the phantom 29 is properly located at the vertical bottom of the radiation emission part 17. At this time, the X-ray film (F in FIG. 6) is installed in the phantom 29.

When the setting of the phantom 29 is finished, radiation is emitted by rotating the radiation emission part 17 while moving the rotating gantry 15. Verifying the accurate movement of the radiotherapy device by checking if the emitted radiation reaches the target point T is the same as mentioned above.

Figure 8A:
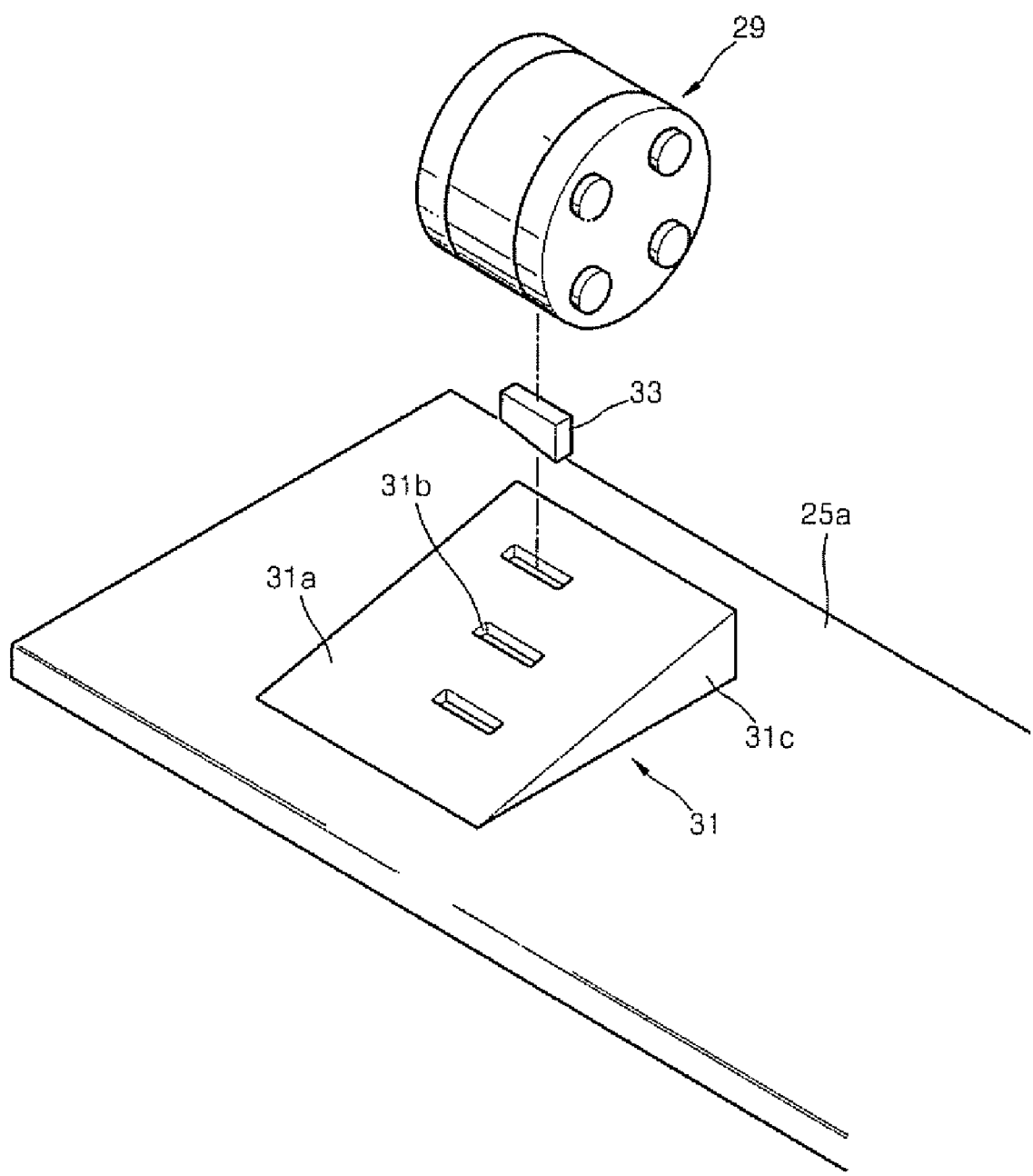
FIGS. 8A and 8B are perspective views describing the principle of separately supporting the phantom shown in FIG. 3 as an inclined status from the top table of the couch.
Figure 8B:
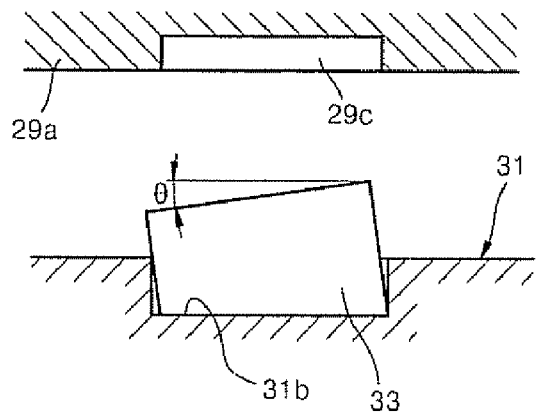

FIGS. 8A and 8B are perspective views illustrating the principle of separately supporting the phantom shown in FIG. 3 on an incline from the top table of the couch.

As shown in FIG. 8A, the phantom is located at a certain height from the flat table 25a when the supporting block 33 is inserted into any fixing groove 31b formed on the tilted plane 31a of the tilted panel 31c and then the supporting block 33 is inserted into the supporting groove 29c formed on the outer circumference of the phantom.

When the phantom 29 is supported by the other fixing groove among a plurality of fixing grooves 31b, the height of the phantom 29 can be changed The height of the phantom from the flat table 25a can be changed as needed by using the tilted base 31.

FIG. 8B is a view for explaining the role of the supporting block 33. Referring to the drawing, the top surface of the supporting block 33 is inserted into the fixing groove 31b and fixed on the bottom surface of the fixing groove so as to be inclined at an angle of θ degrees towards the horizontal plane.

Figure 9:
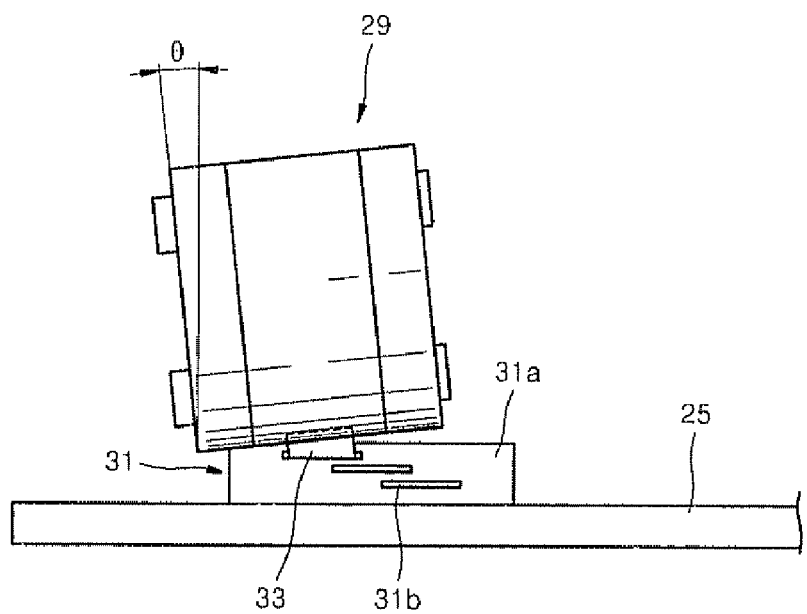
FIG. 9 is a side elevation view illustrating the phantom installed on the base shown in FIG. 8A.

Since the top surface of the supporting block 33 is inclined, the phantom 29 supported by the supporting block 33 is inclined at an angle of θ degrees as shown in FIG. 9.

FIG. 9 is a side view illustrating the phantom installed on the base shown in FIG. 8A.

Referring to the drawing, it is understood that the phantom 29 is separately inclined from the flat table 25*a* by being supported on the tilted base 31 via the supporting block 33. By placing the phantom 29 inclined like this, the quality assurance through the image matching in accordance with the aforementioned principle can be achieved while the CT apparatus and the radiotherapy device are taking tomographic images of the inclined phantom.

Although the exemplary embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A calibration phantom for quality assurance placed on a couch of an image-based radiotherapy apparatus, which includes a computed tomography apparatus and a radiation treatment machine combined with the computed tomography apparatus, and is provided for quality assurance of the computed tomography apparatus and the radiation treatment machine based on an image scanned by the computed tomography apparatus and the radiation treatment machine, the calibration phantom comprising:

a body comprising a cylindrical acryl member having a predetermined diameter, wherein the body has a center hole at a center axis thereof and a plurality of through-holes in outer circumferential portions thereof at a predetermined interval from the center hole;

round stick-type density bars inserted into corresponding ones of the through-holes of the body, with cross-sectional shapes thereof appearing on the image scanned by the computed tomography apparatus and the radiotherapy apparatus, the density bars made of materials each with different densities;

an acrylic cover detachably coupled with both ends of the body and having the same diameter as the body; and a plurality of bolts closely fastening the body with the cover by extending through the cover and the body and coupling with nuts, with cross-sectional shapes thereof appearing on the image scanned by the computed tomography apparatus and the radiotherapy apparatus, the bolts each made of different materials.

2. The calibration phantom for quality assurance according to claim 1, further comprising a plug inside the center hole, wherein the plug has disk-shaped multiple holes having different diameters, which is used for inspecting a resolution of the computed tomography apparatus.

3. The calibration phantom for quality assurance according to claim 1, further comprising a bead in an internal central area of the center hole, wherein a cross section of the bead appears as a central point of the phantom on the image scanned by the computed tomography apparatus and radiotherapy device.

4. The calibration phantom for quality assurance according to claim 1, wherein the density bars and the bolts are made of any one selected from the group consisting of polyacetal, monomer cast nylon, acryl, polyethylene, polycarbonate, polytetrafluoroethylene, polypropylene, and polyvinyl chloride.

5. The calibration phantom for quality assurance according to claim 1, further comprising a base at the bottom of the phantom so as to support the phantom on the couch.

6. The calibration phantom for quality assurance placed on a couch of an image-based radiotherapy apparatus, which includes a computed tomography apparatus and a radiation treatment machine combined with the computed tomography apparatus, and is provided for quality assurance of the computed tomography apparatus and the radiation treatment machine based on an image scanned by the computed tomography apparatus and the radiation treatment machine, the calibration phantom comprising:

a body comprising a cylindrical acryl member having a predetermined diameter, wherein the body has a center hole at a center axis thereof and a plurality of through-holes in outer circumferential portions thereof at a predetermined interval from the center hole, said center hole comprising a plug comprising disk-shaped multiple holes having different diameters, further comprising a bead in an internal central area of the center hole, wherein a cross section of the bead appears as a central point of the phantom on the image scanned by the computed tomography apparatus and radiotherapy device;

round stick-type density bars inserted into corresponding ones of the through-holes of the body, with cross-sectional shapes thereof appearing on the image scanned by the computed tomography apparatus and the radiotherapy apparatus, the density bars made of materials each with different densities and wherein the density bars and the bolts are made of any one selected from the group consisting of polyacetal, monomer cast nylon, acryl, polyethylene, polycarbonate, Teflon, polypropylene, and polyvinyl chloride;

an acrylic cover detachably coupled with both ends of the body and having the same diameter as the body;

a plurality of bolts closely fastening the body with the cover by extending through the cover and the body and coupling with the nuts, with cross-sectional shapes thereof appearing on the image scanned by the computed tomography apparatus and the radiotherapy apparatus, the bolts each made of different materials;

a base at the bottom of the phantom so as to support the phantom on the couch and further wherein the base has an inclined plane at a predetermined angle towards a flat table of the couch;

a plurality of fixing grooves formed on the inclined plane to support the phantom on the inclined plane; and a supporting block provided to support the phantom on the base, wherein the supporting block is inserted into the fixing groove in a protruding state from the inclined plane and is coupled into the groove of the outer surface of the phantom.

7. The calibration phantom for quality assurance according to claim 6, wherein a top surface of the supporting block protruding toward a top portion of the base is inclined at a predetermined angle towards the flat table in order to tilt the phantom placed on the base at a predetermined angle.

* * * * *